United States Patent [19]
Hashimoto et al.

[11] Patent Number: 4,808,726
[45] Date of Patent: Feb. 28, 1989

[54] PROCESS FOR PREPARATION OF GUANIDINE DERIVATIVE

[75] Inventors: Isao Hashimoto, Iwakuni; Ikuo Tomino, Ohtake; Houji Kato, Waki; Noriaki Kihara, Iwakuni; Teruaki Mukaiyama, Tokyo, all of Japan

[73] Assignee: Mitsui Petrochemical Industries, Ltd., Tokyo, Japan

[21] Appl. No.: 91,849

[22] Filed: Sep. 1, 1987

[30] Foreign Application Priority Data

Sep. 1, 1986 [JP] Japan ................................ 61-203639

[51] Int. Cl.$^4$ .......................................... C07D 233/54
[52] U.S. Cl. ................................................... 548/342
[58] Field of Search ......................................... 548/342

[56] References Cited

U.S. PATENT DOCUMENTS 4,602,093  7/1986  Baldwin et al. ..................... 548/342

FOREIGN PATENT DOCUMENTS 6092257  10/1983  Japan .................................. 548/342
455991   2/1977   Spain .................................. 548/342
2025969  1/1980   United Kingdom ............... 548/342

Primary Examiner—John M. Ford
Assistant Examiner—Robert C. Whittenbaugh
Attorney, Agent, or Firm—Sherman and Shalloway

[57] ABSTRACT

N-cyano-N'-methyl-N''-(2-(5-methyl-4-imidazolylmethylthio)ethyl)guanidine (Cimetidine), which is valuable as an agent for controlling secretion of gastric acid, is prepared in a high yield by reacting N-cyano-N'-methyl-N''-(2-(butane-2,3-dionyl)thioethyl)-guanidine as the starting compound with an ammonium salt of a carboxylic acid and formaldehyde.

17 Claims, No Drawings

PROCESS FOR PREPARATION OF GUANIDINE DERIVATIVE

BACKGROUND OF THE INVENTION (1) Field of the Invention

The present invention relates to a process for the preparation of N-cyano-N'-methyl-N''-(2-(5-methyl-4-imidazolylmethylthio)ethyl)guanidine (Cimetidine; often referred to as "Cimetidine" hereinafter) valuable as an agent for controlling secretion of gastric acid. More particularly, the present invention relates to a process for preparing Cimetidine in a high yield from N-cyano-N'-methyl-N''-(2-(butane-2,3-dionyl)thioethyl)guanidine.

(2) Description of the Prior Art

Several processes for the preparation of Cimetidine have been known, and a process for preparing Cimetidine through N-cyano-N'-methyl-N''-(2-(butane-2,3-dionyl)thioethyl guanidine is disclosed in Spanish Pat. No. 455,991, British Pat. No. 2,025,969 and Japanese Patent Application Laid-Open Specification No. 92257/85 and this process is advantageous in that Cimetidine can be prepared from cheap starting materials such as ammonia and formaldehyde through a small number of steps. However, in the case where Cimetidine is prepared by reacting N-cyano-N'-methyl-N''-(2-(butane-2,3-dionyl)thioethyl)guanidine with aqueous ammonia and an aqueous solution of formalin, as taught in Japanese Patent Application Laid-Open Specification No. 92257/85, the yield of intended Cimetidine is low (7.7%) and this is a serious defect.

SUMMARY OF THE INVENTION

We made research with a view to improving the yield in the above-mentioned imidazole ring-forming reaction, and as the result, we found a process capable of providing Cimetidine in a much higher yield than in the conventional processes and we have now completed the present invention.

More specifically, in accordance with the present invention, there is provided a process for the preparation of N-cyano-N'-methyl-N''-(2-(5-methyl-4-imidazolylmethylthio)ethyl)guanidine represented by the following formula I:

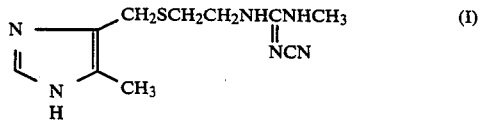

which comprises reacting N-cyano-N'-methyl-N''-(2-(butane-2,3-dionyl)thioethyl)guanidine with an ammonium salt of a carboxylic acid and formaldehyde.

In the preparation of Cimetidine from N-cyano-N'-methyl-N''-(2-(butane-2,3-dionyl)thioethyl)guanidine, according to the present invention, by reacting the starting compound with an ammonium salt of a carboxylic acid and formaldehyde, intended Cimetidine can be obtained in a yield at least about 6 times as high as the yield attained in the conventional technique of reacting the starting compound with aqueous ammonia and an aqueous solution of formalin.

DETAILED DESCRIPTION OF THE PREFERRED EMBODIMENT

N-cyano-N'-methyl-N''-(2-(butane-2,3-dionyl)thioethyl)guanidine used as the starting compound in the present invention can be easily synthesized by reacting N-cyano-N'-methyl-N''-(2-mercaptoethyl)guanidine with diacetyl bromide in the presence of a base according to the teaching of Spanish Pat. No. 455,991.

As the ammonium salt of the carboxylic acid, there are preferably used ammonium salts of monocarboxylic acids having 1 to 8 carbon atoms, such as ammonium formate, ammonium acetate, ammonium monochloroacetate, ammonium dichloroacetate, ammonium trichloroacetate, ammonium methoxyacetate, ammonium propionate, ammonium butyrate, ammonium isobutyrate and ammonium benzoate in the process of the present invention. A purified product of the ammonium salt of the carboxylic acid may be used, but a reaction mixture obtained by reacting a carboxylic acid with aqueous ammonia or ammonia gas in a reaction solvent described hereinafter can be directly used as the ammonium salt.

Any of gaseous formaldehyde, formalin, paraformaldehyde and trioxan can be used as the formaldehyde in the process of the present invention, but formalin and paraformaldehyde are especially preferred.

As the solvent to be used in the process of the present invention, there can be mentioned alcohols such as methanol, ethanol, propanol, isopropanol and butanol, ethers such as diethyl ether, diisopropyl ether, tetrahydrofuran and dioxane, esters such as methyl acetate and ethyl acetate, nitriles such as acetonitrile and propionitrile, and amides such as formamide and N,N-dimethylformamide.

In carrying out the process of the present invention, the molar ratio of the ammonium salt of the carboxylic acid to N-cyano-N'-methyl-N''-(2-(butane-2,3-dionyl)thioethyl)guanidine is from 2 to 20, preferably from 3 to 15, and the molar ratio of formaldehyde to the starting guanidine derivative is from 1 to 10, preferably from 1.2 to 5. In the case where the ammonium salt of the carboxylic acid is formed in the reaction system, a method in which ammonia gas or aqueous ammonia and the carboxylic acid are added to the solvent in a reaction vessel is preferably adopted. In this case, the carboxylic acid/ammonia molar ratio is preferably in the range of from 0.8 to 5. The solvent is used in an amount of 1 to 80 parts by weight, preferably 5 to 70 parts by weight, per part by weight of N-cyano-N'-methyl-N''-(2-(butane-2,3-dionyl)thioethyl)-guanidine.

The reaction temperature is generally −10° to 150° C. and preferably 15° to 120° C. The time required for the reaction depends on the reaction temperature and other conditions, but the reaction is generally 0.2 to 50 hours and preferably 0.3 to 40 hours. After the reaction, the reaction mixture is treated according to a customary post treatment such as extraction, crystallization or column chromatography, whereby intended Cimetidine is obtained.

The process of the present invention will now be described in detail with reference to the following examples.

Examples 1 through 5

A 50 ml flask equipped with a cooler and a thermometer was charged with 121 mg (0.5 millimole) of N-cyano-N'-methyl-N''-(2-(butane-2,3-dionyl)thioethyl)- guanidine, 0.5 ml of a solution of formalin in ethanol (containing 0.75 millimole of formaldehyde), 6 millimoles of an ammonium salt shown in Table 1 and 10 ml of ethanol, and the mixture was stirred under conditions shown in Table 1. The amount of formed Cimetidine was determined under the following conditions by the high-speed liquid chromatography.

Chromatograph: Shimazu LC-6A
Column: Zorbax ODS, 4.6 mm×25 cm
Developing solution: water/methanol/acetic/acid/triethylamine=700/300/0.8/0.8
Flow rate: 1.0 ml/min.
Internal standard: p-acetotoluide The obtained results are shown in Table 1.

TABLE 1

| Example No. | Ammonium Salt | Reaction Temperature (°C.) | Time (hours) | Yield (%) of Cimetidine |
|---|---|---|---|---|
| 1 | $HCO_2NH_4$ | 78 | 1 | 57 |
| 2 | $CH_3CO_2NH_4$ | 25 | 36 | 46 |
| 3 | $CH_3CO_2NH_4$ | 50 | 1 | 50 |
| 4 | $CH_3CO_2NH_4$ | 78 | 1 | 59 |
| 5 | $C_6H_5-CO_2NH_4$ | 78 | 1 | 54 |

Comparative Example 1

To 10 ml of ethanol was added 121 mg (0.5 millimole) of N-cyano-N'-methyl-N''-(2-(butane-2,3-dionyl)thioethyl)guanidine, and 0.36 ml of 28% aqueous ammonia (containing 6 millimoles of ammonia) was added to the mixture with stirring at −10° C. At this temperature, the mixture was stirred for 20 minutes, and 0.5 ml of a solution of formalin in ethanol (containing 0.75 millimole of formaldehyde) was added and the mixture was stirred at −10° C. for 4 hours and then at 25° C. for 12 hours. The reaction mixture was analyzed in the same manner as described in Example 1. It was found that the yield of Cimetidine was 20%. Unreacted N-cyano-N'-methyl-N''-(2-(butane-2,3-dionyl)thioethyl)-guanidine was not detected in the reaction mixture.

Comparative Examples 2 through 4

At 25° C., 121 mg (0.5 millimole) of N-cyano-N'-methyl-N''-(2-(butane-2,3-dionyl)thioethyl)guanidine, 0.36 ml of 28% aqueous ammonia and 0.5 ml of a solution of formalin in ethanol (containing 0.75 millimole of formaldehyde) were added to 10 ml of ethanol, and reaction was carried out under conditions shown in Table 2. The obtained results are shown in Table 2. In each case, unreacted N-cyano-N'-methyl-N''-(2-(butane-2,3-dionyl)thioethyl)guanidine was not detected in the reaction mixture.

TABLE 2

| Comparative Example No. | Reaction Temperature (°C.) | Time (hours) | Yield (%) of Cimetidine |
|---|---|---|---|
| 2 | 25 | 2 | 6 |
| 3 | 50 | 2 | 3 |
| 4 | 78 | 1 | 6 |

Comparative Example 5

At 25° C., 121 mg (0.5 millimole) of N-cyano-N'-methyl-N''-(2-(butane-2,3-dionyl)thioethyl)guanidine, 321 mg (6 millimoles) of ammonium chloride and 0.5 ml of a solution of formalin in ethanol (containing 0.75 millimole of formaldehyde) were added to 10 ml of ethanol, and the mixture was stirred at 78° C. for 1 hour. The reaction mixture was analyzed in the same manner as described in Example 1. It was found that the yield of Cimetidine was 4%. Unreacted N-cyano-N'-methyl-N''-(2-(butane-2,3-dionyl)thioethyl)guanidine was not detected in the reaction mixture.

Examples 6 through 8

The reaction was carried out in the same manner as described in Example 4 except that a carboxylic acid (6 millimoles) shown in Table 3 and 0.36 ml of 28% aqueous ammonia (containing 6 millimoles of ammonia) were added instead of ammonium acetate. The obtained results are shown in Table 3.

TABLE 3

| Example No. | Carboxylic Acid | Yield (%) of Cimetidine |
|---|---|---|
| 6 | $CH_3CO_2H$ | 62 |
| 7 | $CH_3OCH_2CO_2H$ | 70 |
| 8 | $n-C_3H_7CO_2H$ | 59 |

Example 9 through 11

To 10 ml of ethanol were added 121 mg (0.5 millimole) of N-cyano-N'-methyl-N''-(2-(butane-2,3-dionyl)-thioethyl guanidine, 28 mg of 80% paraformaldehyde (0.75 millimole as formaldehyde) and an ammonium salt (6 millimoles) shown in Table 4, and the mixture was stirred under conditions shown in Table 4.

TABLE 4

| Example No. | Ammonium Salt | Reaction Temperature (°C.) | Time (hours) | Yield (%) of Cimetidine |
|---|---|---|---|---|
| 9 | $HCO_2NH_4$ | 25 | 36 | 62 |
| 10 | $CH_3CO_2NH_4$ | 25 | 36 | 65 |
| 11 | $CH_3CO_2NH_4$ | 50 | 1 | 48 |

Example 12

The reaction was carried out in the same manner as described in Example 4 except that propanol (10 ml) was used as the solvent and the reaction temperature was adjusted to 97° C. The yield of Cimetidine was 59%.

Example 13

To 10 ml of isopropanol were added 363 mg (1.5 millimoles) of N-cyano-N'-methyl-N''-(2-(butane-2,3-dionyl)thioethyl)guanidine, 1.39 g (18 millimoles) of ammonium acetate and 84 mg of 80% paraformaldehyde (2.25 millimoles of formaldehyde), and the mixture was stirred at 84° C. for 0.5 hour (the yield of Cimetidine was 57% as determined by the high-speed liquid chromatography). Then, 1 g of sodium carbonate and 10 ml of water were added to the reaction mixture, and the mixture was evaporated to dryness. To the residue was added 20 ml of isopropanol, and insoluble substances were removed by filtration. The filtrate was concentrated and the obtained solid was purified by the silica gel column chromatography (developing solution:

chloroform/methanol=4/1) to obtain 197 mg of a white powder. The white powder was in agreement with the standard reference of Cimetidine in the melting point (140° to 142° C.), mass spectrum, NMR spectrum and IR spectrum (the yield of the isolated product was 52%).

Example 14

To 250 ml of isopropanol was added 12.1 g (50 millimoles) of N-cyano-N'-methyl-N"-(2-(butane-2,3-dionyl)thioethyl)guanidine, 15.4 g (200 millimoles) of ammonium acetate and 5.62 g (150 millimoles) of 80% paraformaldehyde, and the mixture was stirred at 64° C. for 2 hours. When the liquid reaction mixture was analyzed by the high-speed liquid chromatography, it was found that the yield of Cimetidine was 85%.

We claim:

1. A process for the preparation of N-cyano-N'-methyl-N"-(2-(5-methyl-4-imidazolylmethyl thio)ethyl)-guanidine represented by the following formula (I):

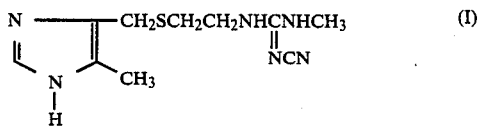

which comprises reacting N-cyano-N'-methyl-N"-(2-(butane-2,3-dionyl)thioethyl)guanidine with an ammonium salt of a carboxylic acid and a source of formaldehyde selected from the group consisting of formaldehyde, formalin, paraformaldehyde and trioxane, wherein the molar ratio of the ammonium salt of the carboxylic acid to the N-cyano-N'-methyl-N"-(2-(butane-2,3-dionyl)thioethyl)-guanidine is from 2 to 20 and the molar ratio of the source of formaldehyde to the N-cyano-N'-methyl-N"-(2-(butane-2,3-dionyl)thioethyl)guanidine is from 1 to 10.

2. The process according to claim 1, wherein the molar ratio of the ammonium salt of the carboxylic acid to the N-cyano-N'-methyl-N"-(2-(butane-2,3-dionyl)thioethyl)guanidine is from 3 to 15.

3. The process according to claim 1, wherein the molar ratio of the source of formaldehyde to the N-cyano-N'-methyl-N"-(2-(butane-2,3-dionyl)thioethyl)-guanidine is from 1.2 to 5.

4. The process according to claim 1, wherein the ammonium salt of the carboxylic acid is an ammonium salt of a monocarboxylic acid having 1 to 8 carbon atoms.

5. The process according to claim 4, wherein the ammonium salt of the monocarboxylic acid is selected from the group consisting of ammonium formate, ammonium acetate, ammonium monochloroacetate, ammonium dichloroacetate, ammonium trichloroacetate, ammonium methoxyacetate, ammonium propionate, ammonium butyrate, ammonium isobutyrate and ammonium benzoate.

6. The process according to claim 1, wherein said formaldehyde is gaseous formaldehyde.

7. The process according to claim 1, wherein said source of formaldehyde is selected from formalin and paraformaldehyde.

8. The process according to claim 1, wherein said reaction is carried out in the presence of a solvent selected from the group consisting of alcohols, ethers, esters, nitriles and amides.

9. The process according to claim 8, wherein said solvent is present in an amount of 1 to 80 parts by weight per part by weight of N-cyano-N'-methyl-N"-(2-(butane-2,3-dionyl)thioethyl)guanidine.

10. The process according to claim 9, wherein said solvent is present in an amount of 5 to 70 parts by weight per part by weight of N-cyano-N'-methyl-N"-(2-(butane-2,3-dionyl)thioethyl)guanidine.

11. The process according to claim 8, wherein said alcohol is selected from the group consisting of methanol, ethanol, propanol, isopropanol and butanol.

12. The process according to claim 8, wherein said ether is selected from the group consisting of diethyl ether, diisopropyl ether, tetrahydrofuran and dioxane.

13. The process according to claim 8, wherein said ester is selected from the group consisting of methyl acetate and ethyl acetate.

14. The process according to claim 8, wherein said nitrile is selected from the group consisting of acetonitrile and propionitrile.

15. The process according to claim 8, wherein said amide is selected from the group consisting of formamide and N,N-dimethylformamide.

16. The process according to claim 1, wherein said reaction is carried out at a temperature of −10° to 150° C.

17. The process according to claim 16, wherein said reaction is carried out at a temperature of 15° to 120° C.

* * * * *